United States Patent [19]

Bieringer

[11] Patent Number: 4,606,634
[45] Date of Patent: Aug. 19, 1986

[54] SYSTEM FOR DETECTING SELECTIVE REFRACTIVE DEFECTS IN TRANSPARENT ARTICLES

[75] Inventor: Robert J. Bieringer, Toledo, Ohio

[73] Assignee: Owens-Illinois, Inc., Toledo, Ohio

[21] Appl. No.: 634,930

[22] Filed: Jul. 27, 1984

[51] Int. Cl.$^4$ .................. G01N 21/41; G01N 21/89
[52] U.S. Cl. .................. 356/240; 250/223 B
[58] Field of Search .................. 356/239, 240, 432; 250/223 B, 562, 572; 358/106

[56] References Cited

U.S. PATENT DOCUMENTS

| | | | |
|---|---|---|---|
| 2,798,605 | 7/1957 | Richards | 356/240 |
| 3,094,214 | 6/1963 | Wyman et al. | 250/223 B |
| 4,017,194 | 4/1977 | Conroy et al. | 356/240 |
| 4,378,493 | 3/1983 | Dorf et al. | 250/223 B |

Primary Examiner—Vincent P. McGraw
Assistant Examiner—S. A. Turner
Attorney, Agent, or Firm—John R. Nelson

[57] ABSTRACT

A system of illuminating a transparent glass article, such as a TV faceplate, for detecting optical defects. The source of illumination is tailored so as to be space invariant and results in producing a plurality of collimated beams which travel in a continuum of different directions. A uniformly illuminated diffuser plate with a mask has the attribute of enhancing refractive defects of a given magnitude while not detecting those of a more gradual refractive nature. The object is viewed with a linear diode array camera of a given acceptance angle.

6 Claims, 16 Drawing Figures

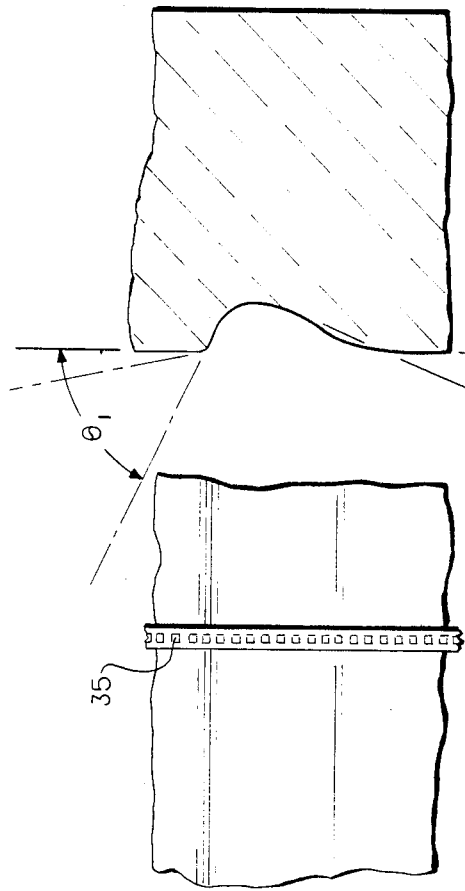
FIG. 3a
FIG. 3b
FIG. 3c
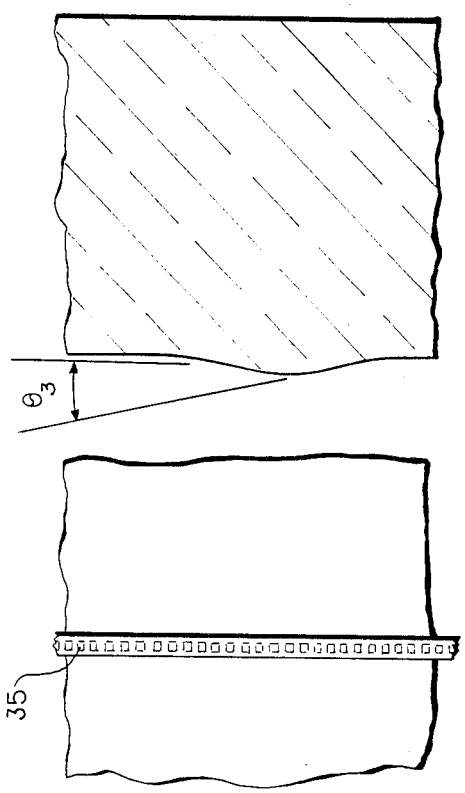
FIG. 4a
FIG. 4b
FIG. 4c

SYSTEM FOR DETECTING SELECTIVE REFRACTIVE DEFECTS IN TRANSPARENT ARTICLES

BACKGROUND OF THE INVENTION

In the detection of optical defects in glass articles, such as bottles or jars, it has been the practice to illuminate the jars, usually with a diffuse backlight, and view the container with an optical or light sensitive pickup. One such arrangement is disclosed in U.S. Pat. No. 4,378,493 dated Mar. 29, 1983. In this patent there is disclosed a system for illuminating the full height of a container placed in an inspection position. The source disclosed consists of a plurality of incandescent bulbs behind a frosted glass plate, thus producing generally a relatively large diffuse source for backlighting the container in the inspection position. With this diffuse backlighting arrangement, the side of the container adjacent the light, which may have refractive defects in it, will not enter into or affect the light emanating from the forward or opposite wall of the container to any appreciable extent. A vertical, linear array camera, focused on the front wall of the container, will provide an image of the wall onto the vertical array of pixels in the camera. The pixels then are serially interrogated and adjacent pixels are compared with respect to their output, which is a function of the light received thereon, and in this manner, light which is reflected by defects in the container wall in the view of the camera, will be made apparent by the output of the linear array. Of course this particular arrangement requires rotation of the container about its vertical axis in order to provide a circumferential scan of the entire container side wall and viewing area, which may also include the neck and shoulder area of the container. In this system, when a reflective defect, such as a check or an absorptive defect, such as a stone, appears in the wall of a container, as that portion of the wall is moved through the viewing area of the camera, the pixels upon which the wall is being focused will see areas of darkness caused by the reflection of the illuminated light out of the line of sight of the pickup. In this way, as previously stated, by comparing the output of adjacent pixels one can determine where the defect lies in a vertical plane and also to a great extent can determine the size of the defect as well. The pixels are scanned at a sufficient rate so that essentially every area of the bottle is viewed and most defects actually will span more than a single scan and will appear in several successive scans.

It should be remembered, however, that the light which reaches the forward wall of the container has come from a diffuse source and therefore is not affected by most light refracting effects in the object. This is particularly apparent when one considers that most optical inspection systems which are looking for dirt in the container use a diffuse source positioned below the upright container so that lettering, such as factory and mold numbers, will not be visible from above the container where the optical transmission analyzer is located.

It has also been the practice to optically detect defects such as checks in various portions of glass articles by focusing a beam of light onto an area of the article at a particular angle and then positioning a pickup, such as a photocell, at approximately a 90° angle with respect to the direction of the focused light. In this arrangement, such as is shown in U.S. Pat. No. 3,245,533, the light will be reflected from the defect onto the photocell, thus indicating the presence of a reflective defect. This has been the typical system for examining the finish and heel portions of glass containers in the past and the focused light will be reflected by a check into the photocell as the container is rotated about its vertical axis, in station, where the inspection setup is provided. It should be understood that the defects which are being detected are those typically termed checks caused usually by thermal shocks during the formation of the container generally by the touching of the hot glass after forming by a cold piece of handling equipment. Generally speaking, checks are reflective if their opposed surface separation is at least a half wave length. If the separation is less than a half wave length, the light would pass through and the defect would not reflect light and therefore not be detectable. Another defect which is picked up by the use of specular, focused light are those surface defects produced in glass containers which will cause the focused light to be refracted out of the direction in which it is being transmitted to the container and the placing of the pickups at positions such that refraction, for example, from a line over finish defect, such as illustrated in U.S. Pat. No. 3,302,787, will be detected.

In the inspection of flat glass articles such as television face plates or architectural glass, it has been customary to illuminate the article with a beam of focused light and then sweep the focused light across the width of the article while moving the article at right angles to the scanning beam. In this way, nearly all of the glass surface will be covered. The light passing through the article is picked up by a complementary scanning photocell. Such a system is shown in U.S. Pat. No. 3,199,401 to Pittsburgh Plate Glass Co. It should be noted that the system requires that an angular illumination be used to avoid reflections that might give erroneous readings. The movement of slightly wavy appearing surfaces into the view of the light and pickup will cause refraction of the focused light and result in the pickup being without illumination during these periods. Whether these are commercially unacceptable becomes a matter of concern, and it would be advantageous to have an inspection system where the defects that are of the type which make the product unsatisfactory for its intended purpose, are enhanced and discriminated from those refractive effects that are not severe.

OBJECTS AND SUMMARY OF THE INVENTION

In view of the foregoing, it is an object of the present invention to provide method and apparatus for inspecting and sorting transparent articles, such as TV faceplates, which are economical to implement due to the special illumination technique used, capable of discrimination and which are effective for sorting acceptable commercial ware from defective unacceptable ware.

In accordance with the present invention, a system is provided for optically illuminating transparent glass objects for the purpose of detecting optical defects in the objects. The disclosed system of illumination provides for a space-invariant illumination of the objects that are moved through the field of view of the optical pickup.

Therefore, it is an object of the present invention to inspect objects for light refractive defects by using a masked diffuse source placed at the focal plane of a lens to produce a plurality of collimated beams traveling in a continuum of different directions with the result of illuminating the object to be inspected with a tailorable distribution of ray directions, or angular spectrum.

It is a further object of the present invention to back illuminate the object, then view the object with a linear array camera and analyze the signals received by the camera so as to detect those defects which are refractive in nature and of a certain slope while not detecting refractive distortions of a more gradual nature.

It is a still further object of the present invention to provide a system of detecting optical defects such as stones and buried blisters in glass objects by back illuminating the object with a space invariant system moving the object relative to the source and observing variations in transmitted light intensity passing out of the object by a line-scan camera.

BRIEF DESCRIPTION OF THE DRAWINGS

FIG. 3(a) is a partial cross-sectional view on an enlarged scale of that portion of FIG. 2 viewed along the line 3—3;

FIG. 3(b) is an enlarged, fragmentary schematic diagram illustrating the optical viewing system of FIG. 1 as viewed along the line 3—3 of FIG. 2;

FIG. 3(c) is a graphic illustration of the transmissivity readings obtained from FIG. 3(b) viewing;

FIG. 4(a) is a cross-sectional view, on an enlarged scale, of a portion of the article being viewed along line 4—4 of FIG. 2;

FIG. 4(b) is an enlarged, schematic view similar to FIG. 3(b) illustrating the viewing of that portion of FIG. 2 along the line 4—4;

FIG. 4(c) is a graphic illustration of the optical transmissivity readings obtained from the viewing of FIG. 4(b);

DETAILED DESCRIPTION OF THE DRAWINGS

Figure 1:
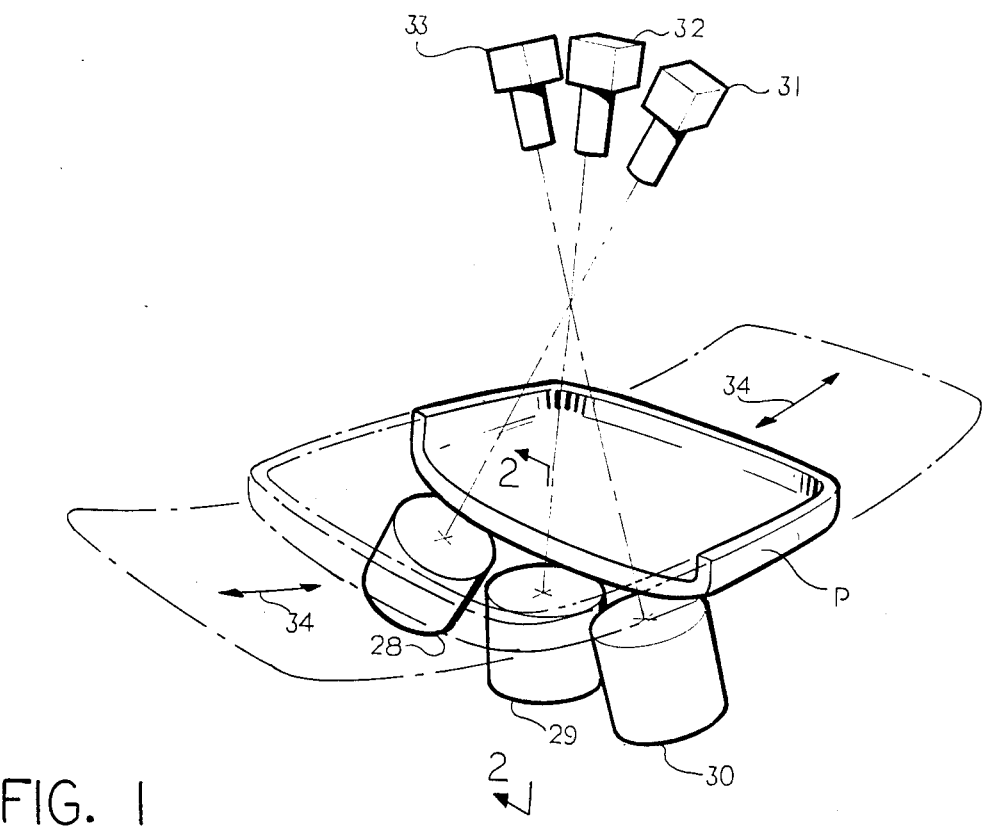
FIG. 1 is a schematic, perspective view of one embodiment of the apparatus of the invention.

In the forming of transparent ware on typical glass forming machines, a number of defects which do not absorb light may appear in the ware. These forming defects generally fall into three categories when dealing with the defects which exhibit surface shape variations. One example of this would be the line over finish defect explained above. Another example are voids which are sometimes termed blisters or seeds, depending on their relative size, and a further example is material inhomogeneities. In general, all of these defects will cause light rays to either be refracted or reflected.

The detection of refractive defects in objects of simple geometry, such as a flat plate glass, would seem to be relatively straightforward. By back illuminating such a plate with a focused light beam and then imaging, in transmitted light, the plate with an optical system of limited acceptance angle, regions of the plate which refract light out of the beam entering the optical system will appear dark. The sensitivity to defects, of such a system, will depend upon the acceptance angle of the imaging optics and on the angularity of the illumination. However, the detection of refractive defects in objects of more complex shapes, such as glass containers, presents a problem of another magnitude. Containers will refract light from a specular beam due simply to their basic geometric shape, not necessarily due to any specific defect. In addition, the inner surface of a glass container is free-formed and therefore this inner surface is subject to considerable surface shape variations in perfectly acceptable commercial ware. The appearance of these surface shape variations will generally obviate techniques such as the one described above for the flat plate.

In the inspection of TV faceplates for optical defects which are of a nature to render the faceplate unacceptable, the inspection begins prior to final polish and one must contend with outside surface crizzles. Crizzles, when illuminated with a beam of limited angular spectrum, cause the light in the transmitted pattern to be deflected due to refraction.

In order to provide an illumination which would be optically detectable, it would appear that a more angularly rich source, such as a diffuse source, would be necessary. As indicated previously, it is known that in detecting defects which absorb light, unwanted effects due to refraction can, to a large extent, be averaged out by using isotropic back illumination and imaging the object in transmission. If one is to inspect, for example, the approximately cylindrical side wall of a transparent container where a source is on one side of the bottle conveying system and the camera is on the opposite side, the illumination of the container will have to be viewed after it has passed through two walls of the container. However, when using a generally diffuse source, the appearance of the container wall closest to the viewing system will not appreciably differ from that which would result with the far wall not present. Thus, for the sake of clarity, you can mentally eliminate the far wall and in essence consider an inspection concept with reference to a system in which essentially only one wall is being viewed. Most machine made glass containers have what is termed a "settle wave" which appears generally below the median height of the container and yet above the heel area. This "settle wave" is produced when the glass is blown from the parison shape into final bottle shape and is due to a condition where the glass in one annular area of the parison adjacent the baffle is normally colder and thus does not expand as evenly as other areas of the parison. This produces, in the side wall of the container, a somewhat thicker annular area in the glass. The settle wave generally is an appearance problem and, if it is not severe, it normally does not affect the commercial ability of the container.

The "settle wave" can be termed a gradual, refractive, optical disturbance in the side wall of the container.

Figure 5:
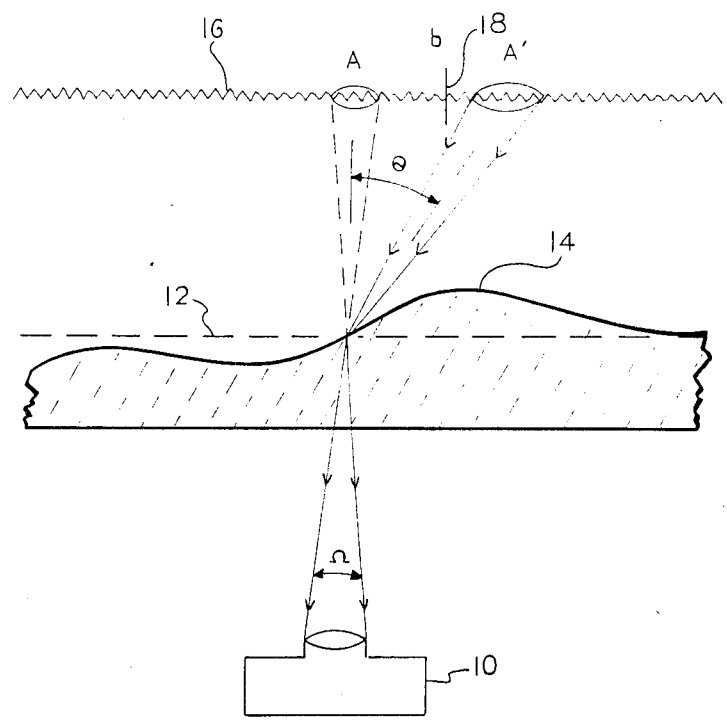
FIG. 5 is a graphic illustration helpful in explaining the optical theory underlying the present invention.

As schematically shown in FIG. 5, which is a representation, in two dimensions, of the transmission of light through a section of a glass article as viewed by a camera 10 having an acceptance angle omega and imaging the vicinity of point C of the article. If the inner surface of the article is planar, that is, as shown by the dashed line 12, the light appearing to come from point C originates at the source area A. If, however, the inner surface is non-planar, as illustrated by the solid line 14, the viewing axis is, in effect, refracted by an angle $\theta$ and light appearing to come from point C actually originates at the source area A'. If the source 16 has uniform brightness and is isotropic, the apparent brightness of point C will be essentially unaffected, in the absence of absorption, by the depicted refraction. On the other hand, this refraction could be detected by masking area A', for example at the right of line 18, thus making this area non-emitting, in which case the image of point C would appear dark against a bright field. Refractive defects are then detected by means of decreases in the apparent transmission of points such as C, as if they were absorptive defects.

The use of masks, however, has limited applicability in defect detection because the use of masks is not space invariant. The appearance of a given defect will depend upon the relative positions of point C and the edge 18 of the mask, thus making the appearance of the defect depend upon its transverse location in the field and upon the longitudinal distance of the object from the mask. Thus, even a moderate refractive error in one portion of the field can produce a reduction in transmission equal to that obtained for a larger refractive error in another portion of the field. Thus, the system is space variant. These limitations can be circumvented, however, by insuring that the apparent transmission of the point C is dependent only upon the angle $\theta$ through which the viewing axis is refracted.

It is suggested, in view of the foregoing, that by back illuminating the object with a source of uniform brightness and of non-isotropic intensity distribution, the light transmission intensity will be independent of the location of the point A' on the source and, thus, the relative positions of point C and A', yielding the desired space invariance. Using a newly devised technique, a spatial intensity distribution is produced at the diffused source and is converted to an angular distribution at the sample side of the lens, the task of selectively rendering invisible the gradual surface variations can be performed optically. Since these variations generally refract the viewing axis through small angles, they are unobservable if the source intensity distribution or angular spectrum is uniform in these small angles.

Figure 2:
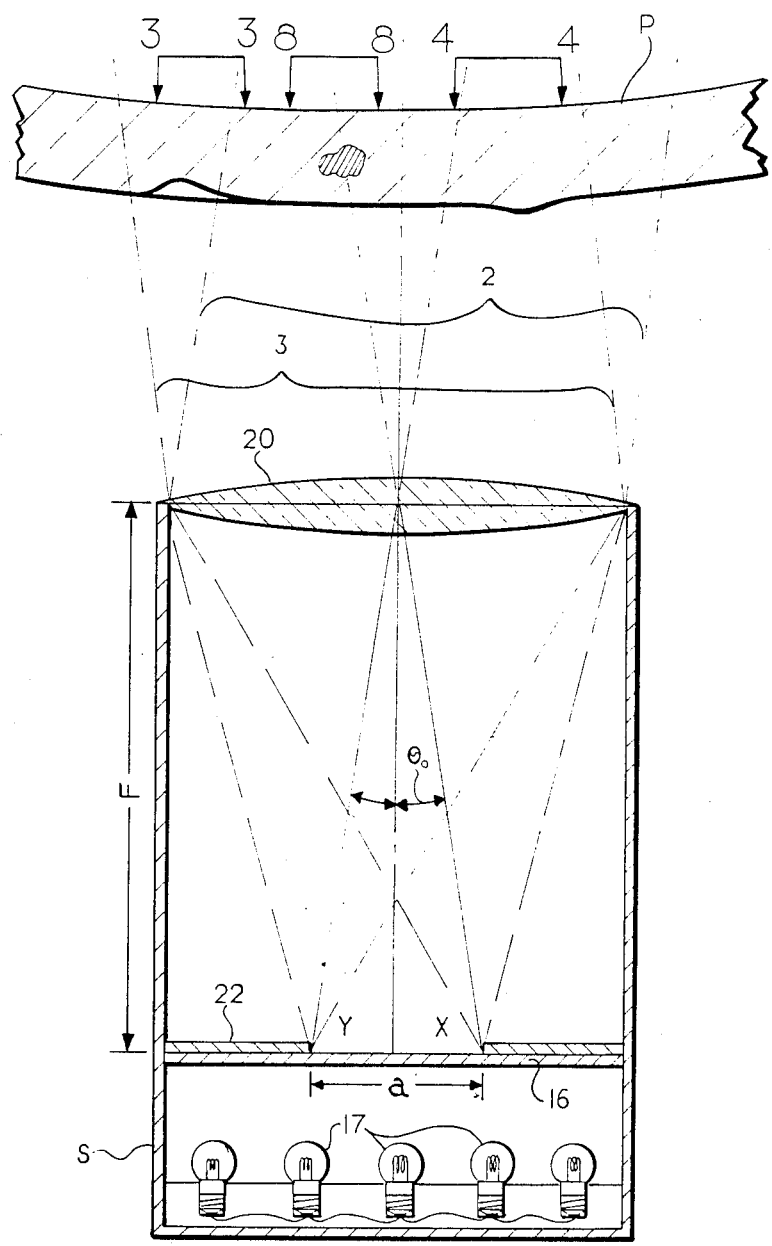
FIG. 2 is a vertical, cross-sectional view of the illuminating system taken at line 2—2 of FIG. 1.

With particular reference to FIG. 2, there is schematically shown the optical implementation of a tailorable source having the desired angular spectrum. A diffuse source S in the form of a frosted plate 16 positioned in front of a plurality of light bulbs 17 is placed a distance F in front of a lens 20 having a focal length F. Each unobstructed point such as X and Y on the source S then results, in a plane in front of the lens, in a collimated beam 3 for X and 2 for Y which extends parallel to the line through the point and the center of the lens. If the source is isotropic and of uniform brightness, each beam will contain the same flux density. If a mask 22 of width $a = 2 F \tan \theta_0$ is placed on the diffuse source, the angular spectrum of illumination in front of the lens will be limited to angles equal to or less than $\pm \theta_0$. Thus, it can be seen by changing mask widths one can easily vary the angle $\theta_0$. In addition, the two dimensional angular spectrum in the plane in front of the lens need not be isotropic, but can be configured essentially arbitrarily by choosing different shapes for the masks.

Figure 6:
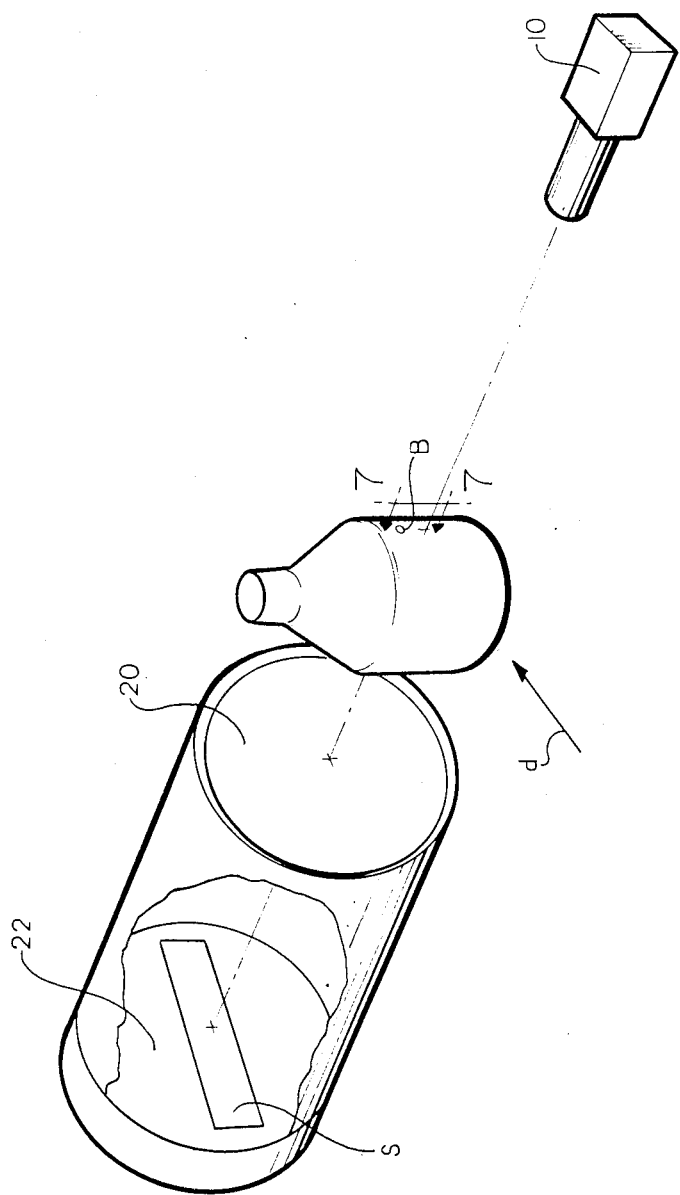
FIG. 6 is a schematic perspective view of the inspection system of the invention, similar to FIG. 1, when viewing a glass container.
Figure 8C:
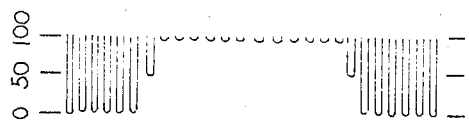
FIG. 8(a) is a cross-sectional view, at line 8—8 of FIG. 2, on an enlarged scale, through the viewing area of an article having a stone therein.
FIG. 8(b) is an enlarged, schematic diagram of the camera viewing area of FIG. 8(a); and, FIG. 8(c) is a camera signal level graph corresponding to FIG. 8(b).

The use of a non-isotropic angular spectrum is particularly useful for inspecting transparent bottles since, in profile, they are not circularly symmetrical. It can thus be seen that with the technique as described with respect to FIG. 2, there is provided a space invariant version of source masking similar to that described for the space variant situation explained previously. The essential effect of the system of illumination is to give an enhanced illumination so that refractive defects of a steep angle are enhanced and can be viewed with greater certainty of detection. The camera 10, since it is a vertical, line scan, linear array, will focus on a line in the space through which the object moves. The light source is made wide in the direction "d" of movement of the object or perpendicular to the axis of the container as shown in FIG. 6, but it can be narrow in the other direction. The light hitting the back side of the object is highly angular and directional in its direction of illumination, whereas if a diffuser were used it would give illumination that would be in all directions. The angular direction of illumination, therefore, is tailored to the physical and optical characteristics of the object being viewed and by selecting the angle of acceptance and the focal length of the lens with respect to the mask, the lens makes the source highly angular in direction.

Each point on the diffuse source 16 will generate a family of rays emanating from the entire surface of the lens 20 and which will be traveling parallel to a line from that point through the center of the lens. Each point on the source will generate such a family with directions defined by the difference in location of the point in relation to the center of the lens. This results in the generation of an angular spectrum of light which is the same for all locations in front of the lens; i.e., space invariant illumination. This spectrum of light angles is the thing being chosen by the illumination system of the invention. You choose this spectrum for giving the greatest enhancement of the types of refractive defects you are wanting to detect while illuminating the gradual sloping irregularities that would normally be refracted by specular light. If the source were very diffuse, all refractive defects would be washed out and you would not see anything. It should be pointed out also that the camera in the present description of the invention is looking at the vertical slices of the object as the object moves through the field of view. The technique of "tailoring" of the light source can also be used in a second imaging situation.

Thus, it can be seen with the foregoing system that the angular spectrum produced by the illumination system of the invention will result in a highly sensitive illumination system for determining the presence of sharp refractive defects while suppressing the appearance of more gradual surface discontinuities that might be present in, for example, a glass container or other transparent glass article being moved through the view of the camera 10.

Turning now specifically to FIG. 1, there is shown the illumination system of the invention being used to illuminate a TV faceplate "P" for detecting selective refractive defects as well as stones, buried blisters, pits and other functional defects in the glass.

Since a TV faceplate is both large in area and curved in both its width and length dimensions, it was determined that the use of three inspection channels would be more suitable. Sources 28, 29 and 30, as shown in detail in FIG. 2, are arranged in side-by-side fashion beneath and across the width of the faceplate P. Each source is positioned with its central axis generally perpendicular to the surface of the portion of the faceplate it is facing. Each source 28, 29 and 30 has a camera 31, 32 and 33, respectively, in alignment therewith for viewing a linear area of the faceplate that is being illuminated by the sources. The linear array in each of the cameras is viewing a portion of a line that extends across the width of the faceplate, excluding the raised edges. In actual practice the faceplate P is supported in a cradle, not shown, and is moved through an arc in the direction of the arrows 34 shown at either end of the faceplate. The center of the arc of movement of the cradle would essentially correspond to the axis of curvature of the faceplate P, in the direction of its length, being inspected. As the faceplate is swung through the arc, all areas of its surface will pass between the sources 28–30 and cameras 31–33 and the full area of the viewing portion of the faceplate will be inspected. It is apparent that by splitting the light source into three sections as shown, a smaller size fresnel lens may be used and the axes of the sources can be displaced to more evenly match the curvature of the faceplate. A single fresnel lens of sufficient size could, however, be used with a source of diffused light for illuminating the entire width of the faceplate.

As can be seen when viewing FIG. 6, the lens 20 is of a size that is large enough to illuminate the entire container being inspected. In order, however, to view the entire circumference of the container, or in particular the edges as viewed in FIG. 6, it would be necessary to pass the container through the viewing area again after it is reoriented 90° about its vertical axis. In this manner, the full area of the container would come under the scrutiny of the inspection system. Obviously, it is necessary to electronically exclude any signals from the pixels in the camera as the edge areas of the container are being viewed. Here again, the mask 22 that is placed over the diffuser may be tailored to the configuration of the container such that the shoulders and neck of the container can be inspected as well. In this case the mask would resemble open butterfly wings with the wide area corresponding to the sloping shoulder area of the container.

With reference to FIGS. 3a and 4a there are shown, in section, two types of surface configurations that may occur in the pressing of faceplates. In FIG. 3a there is a line in the glass with a fairly sharp angle $\theta_1$ at its top edge and a more gradual return slope at angle $\theta_2$ to the general plane of the faceplate. In the case of the angle $\theta_1$, the light will be refracted and the level of the output signal derived from the vertical row of pixels 35 depicted schematically in FIG. 3b. As can be seen, since the angle $\theta_1$ is greater than the angle $\theta_0$ the light is refracted and the pixels that view the sloping surface will not receive any appreciable light. On the other hand, the slope of the angle $\theta_2$ being less than $\theta_0$ will not refract the light from the source and the pixel will receive essentially full illumination.

The surface condition illustrated in FIG. 4(a) is one where a slightly raised area is present with the slope of the area shown by angle $\theta_3$ as being less than $\theta_0$. As in the case of the lower portion of FIG. 3a, the pixels 35 will receive an even amount of illumination and the diagram 4(c) reflects this by showing the level of the signals from the pixels of FIG. 4(b) being all the same.

Turning now specifically to FIGS. 7(a)–(c) and FIGS. 8(a)–(c), there is illustrated in enlarged scale two defects that are of the type that represents a subset of all types of defects which would be detectable by the present inspection system.

Figure 7C:
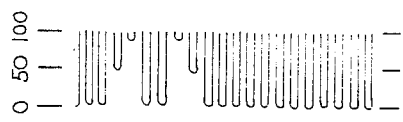
FIG. 7(c) is a camera signal level graph corresponding to FIG. 7(b)
Figure 7B:
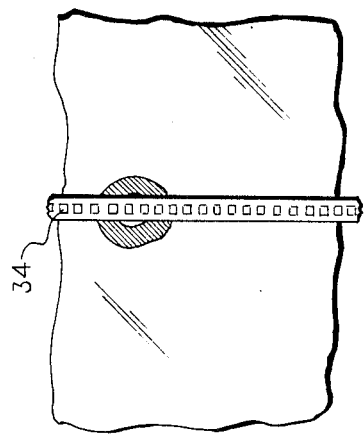
FIG. 7(b) is an enlarged, schematic diagram of the camera viewing area of that portion of the bottle of FIG. 7(a)
Figure 7A:
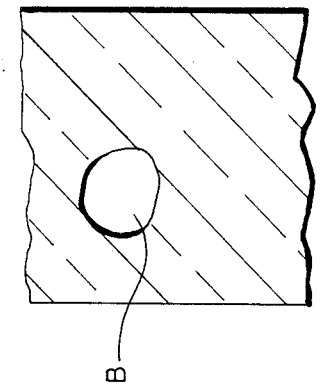
FIG. 7(a) is a cross-sectional view, on an enlarged scale, taken at line 7—7 of FIG. 6 showing an included blister.

In FIG. 7(a), the defect is a buried blister B which is of the type where its slope or angle is such that it will refract incident light at an angle which is greater than the angle of the illumination spectrum. Thus, the refraction of the light from the source of illumination will be refracted out of the normal line of sight of several of the camera pixels and thus the defect is detected. It can be seen, however, when viewing 7(c) that the center of the blister will not deflect the light.

FIG. 7(b) illustrates the lower light intensity that is present at the camera, while 7(c) illustrates the signal level at the camera for each of the pixels 35 illustrated. It should be remembered that the level of light intensity is 100% where there is no refraction or absorption of light by the object being viewed and essentially zero where there happens to be complete refraction, as is the case illustrated in FIGS. 3(a) and 7(a). The lower part of the defect in FIG. 3(a) is of a more gradual slope and the spectrum of the incident light has been chosen so that the incident light is not refracted by such a gradual slope to any detectable extent.

Figure 8B:
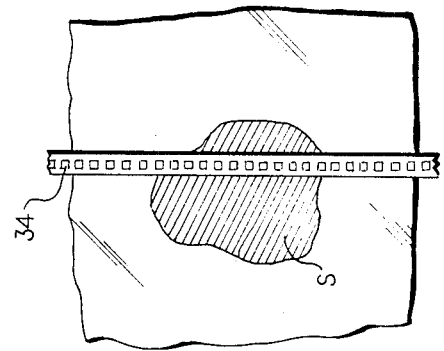
Figure 8A:
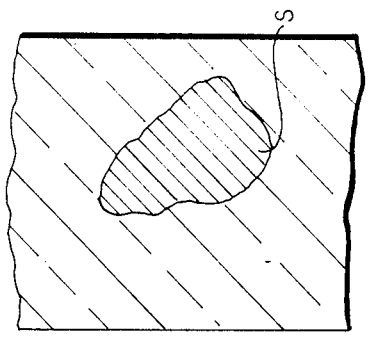

In FIG. 8(a), there is illustrated a defect such as a stone "S" which blocks out the light entirely, since a stone is an opaque inhomogeneity found in some glasses where the ingredients have not totally melted. A stone has the property of forming a stress concentrator and thus becomes a source of fracture from physical impacts or thermal shocks. Thus, glass containers having stones should be rejected whenever detected to avoid costly failures, either in a commercial filling line or at the point of sale. Obviously, when stones are present in a TV faceplate, it is a functional defect which is not tolerated. The blister of FIG. 7(a) and the stone of FIG. 8(a) are both objectionable since they will be apparent to a viewer of the TV whose faceplate contains either defect.

The level of illumination at the camera is illustrated in FIGS. 8(b) and (c) where the effect is that more than one pixel 34 is masked entirely.

The foregoing is a description of several embodiments of the invention where illumination of an object to be inspected is made to be space invariant so that, regardless of where the object is positioned in the field of illumination, it will be given the same level of light intensity and can be viewed with a camera that is, therefore, not sensitive to object position or movement through the field of view of the camera.

What is claimed:

1. Method of inspecting transparent objects for refractive defects comprising producing a generally planar source of diffuse light of uniform brightness, positioning a lens of focal length F greater than 0 in front of the source thereby producing in front of the lens, an angular spectrum of beams that originate from points on the source that are of the same flux density, placing a mask over the source to limit the angular spectrum of illumination in front of the lens to angles where the intensity distribution is uniform and equal to or less than the angle $\theta_o$ between a line extending from the edge of the mask through the center of the lens and the axis of the lens, moving objects to be inspected normal to the lens axis in front of the lens, thereby optically enhancing refractive defects having angles greater than $\theta_o$ and discriminating defects from gradual refractive variations having angles less than $\theta_o$, and viewing the objects with a linear array camera focused on the surface of the object to thereby detect those refractive defects having angles greater than $\theta_o$ by variations in the level of light received by the camera.

2. The method of inspecting transparent articles such as glass containers for optically refractive defects having steep acceptance angles and discriminating against more gradual refractive variations wherein the articles are backlighted as they are moved in a linear upright path in front of a viewing camera having a vertical linear array of pixels for receiving light focused from the vertical wall of the article, the improvement in the backlighting of the article comprising the steps of forming a wide source of diffuse illumination in back of the article, said source having uniform brightness over its surface, placing a convex or Fresnel lens in front of the source at a distance from the source so as to produce an angular spectrum of collimated light coming from the lens in the direction of the path of movement of the article, and limiting the angle of illumination of the source to the lens to angles steeper than the angle of the gradual refractive variations that are to be discriminated.

3. An apparatus for inspecting glass articles for refractive defects of a predetermined severity wherein the glass articles are illuminated from the back as they move through an inspection zone where they are viewed from the front by a camera having a linear, vertical, array of light sensitive pixels, the improvement in the illumination of the glass articles to enhance detection of the refractive defects comprising a source of diffuse light having a surface with uniform brightness, a convex lens in front of the source spaced therefrom a distance so as to produce a spectrum of collimated light extending from the lens through the inspection zone to thereby provide space invariant illumination to the articles which will be refracted from the field of view of the camera due to refractive defects of a predetermined severity.

4. The improvement of claim 3 further including a mask over the peripheral portions of said source, said mask limiting the angle of collimation of said light spectrum to render the illumination less sensitive to gradual refractive variations in the article.

5. The improvement of claim 4 wherein said glass articles are TV faceplates and including a plurality of sources of diffuse light with each source illuminating a different portion of the faceplate.

6. The improvement of claim 5 further including a plurality of cameras each viewing a different illuminated portion of the faceplate.

* * * * *